(12) United States Patent
  Dusan

(10) Patent No.: US 10,761,575 B2
(45) Date of Patent: *Sep. 1, 2020

(54) DETECTING A GESTURE MADE BY A PERSON WEARING A WEARABLE ELECTRONIC DEVICE

(71) Applicant: Apple Inc., Cupertino, CA (US)

(72) Inventor: Sorin V. Dusan, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/366,677

(22) Filed: Mar. 27, 2019

(65) Prior Publication Data
US 2019/0220069 A1 Jul. 18, 2019

Related U.S. Application Data

(63) Continuation of application No. 15/118,053, filed as application No. PCT/US2014/015829 on Feb. 11, 2014, now Pat. No. 10,254,804.

(51) Int. Cl.
  *G06F 1/16* (2006.01)
  *A61B 5/11* (2006.01)
  (Continued)

(52) U.S. Cl.
  CPC ............. *G06F 1/1694* (2013.01); *A61B 5/11* (2013.01); *A61B 5/681* (2013.01); *A61B 5/6824* (2013.01); *A63B 24/0062* (2013.01); *G04C 3/002* (2013.01); *G06F 1/163* (2013.01); *G06F 3/017* (2013.01); *G06F 3/16* (2013.01); *G09B 5/02* (2013.01); *A61B 2562/0219* (2013.01); *A61B 2562/0223* (2013.01); *A63B 2220/833* (2013.01)

(58) Field of Classification Search
  CPC . A61B 5/0452; A61B 5/0408; A61B 5/04012; G06F 3/167; G06F 3/011; G06F 3/017
  USPC .................................................. 702/127, 141
  See application file for complete search history.

(56) References Cited

U.S. PATENT DOCUMENTS 6,996,428 B2  2/2006 Kislov et al.
7,486,386 B1  2/2009 Holcombe
(Continued)

FOREIGN PATENT DOCUMENTS

CN   1572252    2/2005
CN   102483608  5/2012
(Continued)

OTHER PUBLICATIONS

Dozza et al., "A Portable Audio-biofeedback System to Improve Postural Control," Proceedings of the 26th Annual International Conference of the IEEE EMBS, San Francisco, CA, Sep. 1-5, 2004, pp. 4799-4802.

(Continued)

*Primary Examiner* — An H Do
(74) *Attorney, Agent, or Firm* — Brownstein Hyatt Farber Schreck, LLP

(57) ABSTRACT

An electronic device that can be worn on a limb of a user can include a processing device and one or more position sensing devices operatively connected to the processing device. The processing device can be adapted to determine which limb of the user is wearing the electronic device based on one or more signals received from at least one position sensing device.

20 Claims, 10 Drawing Sheets

(51) Int. Cl.

| | | |
|---|---|---|
| G06F 3/16 | (2006.01) | |
| A61B 5/00 | (2006.01) | |
| G06F 3/01 | (2006.01) | |
| G04C 3/00 | (2006.01) | |
| A63B 24/00 | (2006.01) | |
| G09B 5/02 | (2006.01) | |

(56) References Cited

U.S. PATENT DOCUMENTS

| | | |
|---|---|---|
| 7,729,748 B2 | 6/2010 | Florian |
| 7,822,469 B2 | 10/2010 | Lo |
| 7,915,601 B2 | 3/2011 | Setlak et al. |
| 7,957,762 B2 | 6/2011 | Herz et al. |
| 8,954,135 B2 | 2/2015 | Yuen et al. |
| 8,988,372 B2 | 3/2015 | Messerschmidt et al. |
| 9,042,971 B2 | 5/2015 | Brumback et al. |
| 9,100,579 B2 | 8/2015 | Schatvet et al. |
| 9,348,322 B2 | 5/2016 | Fraser et al. |
| 9,427,191 B2 | 8/2016 | LeBoeuf |
| 9,485,345 B2 | 11/2016 | Dantu |
| 9,557,716 B1 | 1/2017 | Inamdar |
| 9,620,312 B2 | 4/2017 | Ely et al. |
| 9,627,163 B2 | 4/2017 | Ely et al. |
| 9,723,997 B1 | 8/2017 | Lamego |
| 9,737,221 B2 | 8/2017 | Sato |
| 9,848,823 B2 | 12/2017 | Raghuram et al. |
| 10,123,710 B2 | 11/2018 | Gassoway et al. |
| 10,126,194 B2 | 11/2018 | Lee |
| 10,254,804 B2 * | 4/2019 | Dusan .................. G04C 3/002 |
| 2011/0015496 A1 | 1/2011 | Sherman et al. |
| 2013/0310656 A1 | 11/2013 | Lim |
| 2015/0275832 A1 | 10/2015 | Kontani et al. |
| 2016/0058309 A1 | 3/2016 | Han |
| 2016/0058375 A1 | 3/2016 | Rothkopf |
| 2016/0198966 A1 | 7/2016 | Uernatsu et al. |
| 2016/0242659 A1 | 8/2016 | Yamashita et al. |
| 2016/0338598 A1 | 11/2016 | Kegasawa |
| 2016/0338642 A1 | 11/2016 | Parara et al. |
| 2016/0349803 A1 | 12/2016 | Dusan |
| 2016/0378071 A1 | 12/2016 | Rothkopf |
| 2017/0011210 A1 | 1/2017 | Cheong et al. |
| 2017/0090599 A1 | 3/2017 | Kuboyama et al. |
| 2017/0181644 A1 | 6/2017 | Meer et al. |
| 2017/0230754 A1 | 8/2017 | Dusan |
| 2017/0354332 A1 | 12/2017 | Lamego |
| 2018/0235542 A1 | 8/2018 | Yun et al. |
| 2019/0072912 A1 | 3/2019 | Pandya et al. |
| 2019/0090806 A1 | 3/2019 | Harrison-Noonan et al. |
| 2019/0101870 A1 | 4/2019 | Pandya et al. |

FOREIGN PATENT DOCUMENTS

| | | |
|---|---|---|
| CN | 203732900 | 7/2014 |
| CN | 104050444 | 9/2014 |
| CN | 105339871 | 2/2016 |
| CN | 205121417 | 3/2016 |
| CN | 105556433 | 5/2016 |
| CN | 105955519 | 9/2016 |
| CN | 106236051 | 12/2016 |
| CN | 106462665 | 2/2017 |
| CN | 206209589 | 5/2017 |
| JP | 2001145607 | 5/2001 |
| JP | 2009519737 | 5/2009 |
| KR | 20110012784 | 2/2011 |
| KR | 1020160145284 | 12/2016 |
| TW | 201610621 | 3/2016 |
| TW | 201621491 | 6/2016 |
| WO | WO 15/030712 | 3/2015 |
| WO | WO 16/204443 | 12/2016 |

OTHER PUBLICATIONS

Ohgi et al., "Stroke phase discrimination in breaststroke swimming using a tri-axial acceleration sensor device," *Sports Engineering*, vol. 6, No. 2, Jun. 1, 2003, pp. 113-123.

Zijlstra et al., "Assessment of spatio-temporal gait parameters from trunk accelerations during human walking," *Gait & Posture*, vol. 18, No. 2, Oct. 1, 2003, pp. 1-10.

Onizuka et al., Head Ballistocardiogram Based on Wireless Multi-Location Sensors, 2015 EEE, pp. 1275-1278.

U.S. Appl. No. 16/118,254, filed Aug. 30, 2018, Harrison Noonan et al.

U.S. Appl. No. 16/118,282, filed Aug. 30, 2018, Clavelle et al.

U.S. Appl. No. 16/193,836, filed Nov. 16, 2018, Pandya et al.

* cited by examiner

DETECTING A GESTURE MADE BY A PERSON WEARING A WEARABLE ELECTRONIC DEVICE

CROSS-REFERENCE TO RELATED APPLICATIONS

This application is a continuation of U.S. patent application Ser. No. 15/118,053, filed on Aug. 10, 2016, and entitled "Detecting the Limb Wearing a Wearable Electronic Device," which is a 35 U.S.C. § 371 application of PCT/US2014/015829, filed on Feb. 11, 2014, and entitled "Detecting the Limb Wearing a Wearable Electronic Device," both of which are incorporated by reference as if fully disclosed herein.

TECHNICAL FIELD

The present invention relates to electronic devices, and more particularly to wearable electronic devices. Still more particularly, the present invention relates to detecting the limb of a user that is wearing a wearable electronic device based on at least one signal from one or more position sensing devices.

BACKGROUND

Portable electronic devices such as smart telephones, tablet computing devices, and multimedia players are popular. These electronic devices can be used for performing a wide variety of tasks and in some situations, can be worn on the body of a user. As an example, a portable electronic device can be worn on a limb of a user, such as on the wrist, arm, ankle, or leg. Knowing whether the electronic device is worn on the left or right limb can be helpful or necessary information for some portable electronic devices or applications. For example, it can be necessary to know whether the electronic device is worn on a left or right limb when the electronic device includes one or more biometric applications, such as an electrocardiography application or a medical measurement or diagnostic application.

SUMMARY

In one aspect, a wearable electronic device can include one or more position sensing devices and a processing device. A processor-implemented method for determining a limb wearing the wearable electronic device can include receiving one or more signals from at least one position sensing device for a given period of time, and analyzing at least one signal to determine the limb wearing the wearable electronic device. In one embodiment, one or more limb gestures and/or a limb positions may be recognized and the limb wearing the electronic device is determined based on the recognized limb gesture(s) and/or position(s). Examples of position sensing devices include, but are not limited to, an accelerometer, a gyroscope, and/or a magnetometer. The at least one signal can be processed by the processing device prior to analyzing the signal or signals. For example, a histogram can be produced, or a two-dimensional or three-dimensional plot can be created based on the at least one signal. In one embodiment, a pattern recognition algorithm can be performed on the at least one signal to determine which limb of the user is wearing the electronic device.

In another aspect, an electronic device that can be worn on a limb of a user can include a processing device and one or more position sensing devices operatively connected to the processing device. The processing device may be adapted to determine which limb of the user is wearing the electronic device based on one or more signals received from at least one position sensing device. In one embodiment, one or more limb gestures and/or a limb positions may be recognized and the limb wearing the electronic device is determined based on the recognized limb gesture(s) and/or position(s).

And in yet another aspect, a system can include an electronic device that can be worn on a limb of a user. The electronic device can include a processing device and one or more position sensing devices operatively connected to the processing device. A display and a memory can each be operatively connected to, or in communication with the processing device. The display and/or the memory can be included in the wearable electronic device or can be separate from the electronic device. The memory may be adapted to store one or more applications. The processing device can be adapted to determine which limb of the user is wearing the electronic device based on one or more signals received from at least one position sensing device. The processing device may also be adapted to provide data to at least one application based on the limb determined to be wearing the electronic device.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures

DETAILED DESCRIPTION

Figure 1:
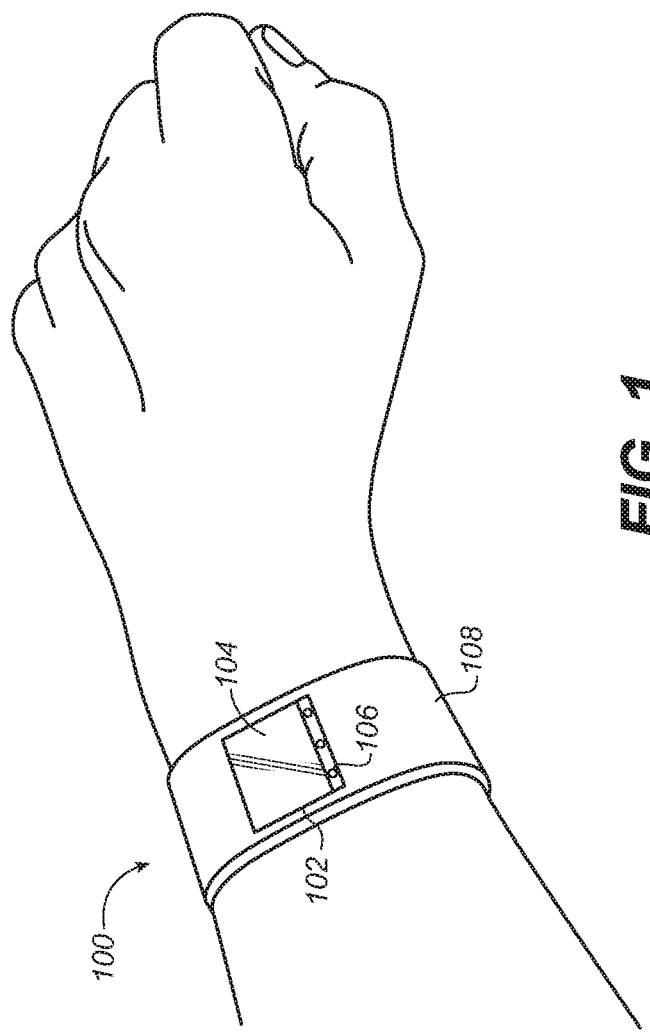
FIG. 1 is a perspective view of one example of a wearable electronic device that can include, or be connected to one or more position sensing devices.

Embodiments described herein provide an electronic device that can be worn on a limb of a user. The electronic device can include a processing device and one or more position sensing devices operatively connected to the processing device. Additionally or alternatively, one or more position sensing device can be included in the band used to attach the wearable electronic device to the limb and operatively connected to the processing device. And in some embodiments, a processing device separate from the wearable electronic device can be operatively connected to the position sensing device(s). The processing device can be adapted to determine which limb of the user is wearing the electronic device based on one or more signals received from at least one position sensing device. For example, in one embodiment a limb gesture and/or a limb position may be recognized and the limb wearing the electronic device determined based on the recognized limb gesture and/or position.

A wearable electronic device can include any type of electronic device that can be worn on a limb of a user. The wearable electronic device can be affixed to a limb of the human body such as a wrist, an ankle, an arm, or a leg. Such electronic devices include, but are not limited to, a health or fitness assistant device, a digital music player, a smart telephone, a computing device or display, and a device that provides time. In some embodiments, the wearable electronic device is worn on a limb of a user with a band that attaches to the limb and includes a holder or case to detachably or removably hold the electronic device, such as an armband, an ankle bracelet, a leg band, and/or a wristband. In other embodiments, the wearable electronic device is permanently affixed or attached to a band, and the band attaches to the limb of the user.

As one example, the wearable electronic device can be implemented as a wearable health assistant that provides health-related information (whether real-time or not) to the user, authorized third parties, and/or an associated monitoring device. The device may be configured to provide health-related information or data such as, but not limited to, heart rate data, blood pressure data, temperature data, blood oxygen saturation level data, diet/nutrition information, medical reminders, health-related tips or information, or other health-related data. The associated monitoring device may be, for example, a tablet computing device, phone, personal digital assistant, computer, and so on.

As another example, the electronic device can be configured in the form of a wearable communications device. The wearable communications device may include a processor coupled with or in communication with a memory, one or more communication interfaces, output devices such as displays and speakers, and one or more input devices. The communication interface(s) can provide electronic communications between the communications device and any external communication network, device or platform, such as but not limited to wireless interfaces, Bluetooth interfaces, USB interfaces, Wi-Fi interfaces, TCP/IP interfaces, network communications interfaces, or any conventional communication interfaces. The wearable communications device may provide information regarding time, health, statuses or externally connected or communicating devices and/or software executing on such devices, messages, video, operating commands, and so forth (and may receive any of the foregoing from an external device), in addition to communications.

Any suitable type of position sensing device can be included in, or connected to a wearable electronic device. By way of example only, a position sensing device can be one or more accelerometers, gyroscopes, magnetometers, proximity, and/or inertial sensors. Additionally, a position sensing device can be implemented with any type of sensing technology, including, but not limited to, capacitive, ultrasonic, inductive, piezoelectric, and optical technologies.

Referring now to FIG. 1, there is shown a perspective view of one example of a wearable electronic device that can include, or be connected to one or more position sensing devices. In the illustrated embodiment, the electronic device 100 is implemented as a wearable computing device. Other embodiments can implement the electronic device differently. For example, the electronic device can be a smart telephone, a gaming device, a digital music player, a device that provides time, a health assistant, and other types of electronic devices that include, or can be connected to a position sensing device(s).

The wearable electronic device 100 includes an enclosure 102 at least partially surrounding a display 104 and one or more buttons 106 or input devices. The enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. One button 106 can take the form of a home button, which may be a mechanical button, a soft button (e.g., a button that does not physically move but still accepts inputs), an icon or image on a display or on an input region, and so on. Further, in some embodiments, the button or buttons 106 can be integrated as part of a cover glass of the electronic device.

The wearable electronic device 100 can be permanently or removably attached to a band 108. The band 108 can be made of any suitable material, including, but not limited to, leather, metal, rubber or silicon, fabric, and ceramic. In the illustrated embodiment, the band is a wristband that wraps around the user's wrist. The wristband can include an attachment mechanism (not shown), such as a bracelet clasp, Velcro, and magnetic connectors. In other embodiments, the band can be elastic or stretchy such that it fits over the hand of the user and does not include an attachment mechanism.

Figure 2:
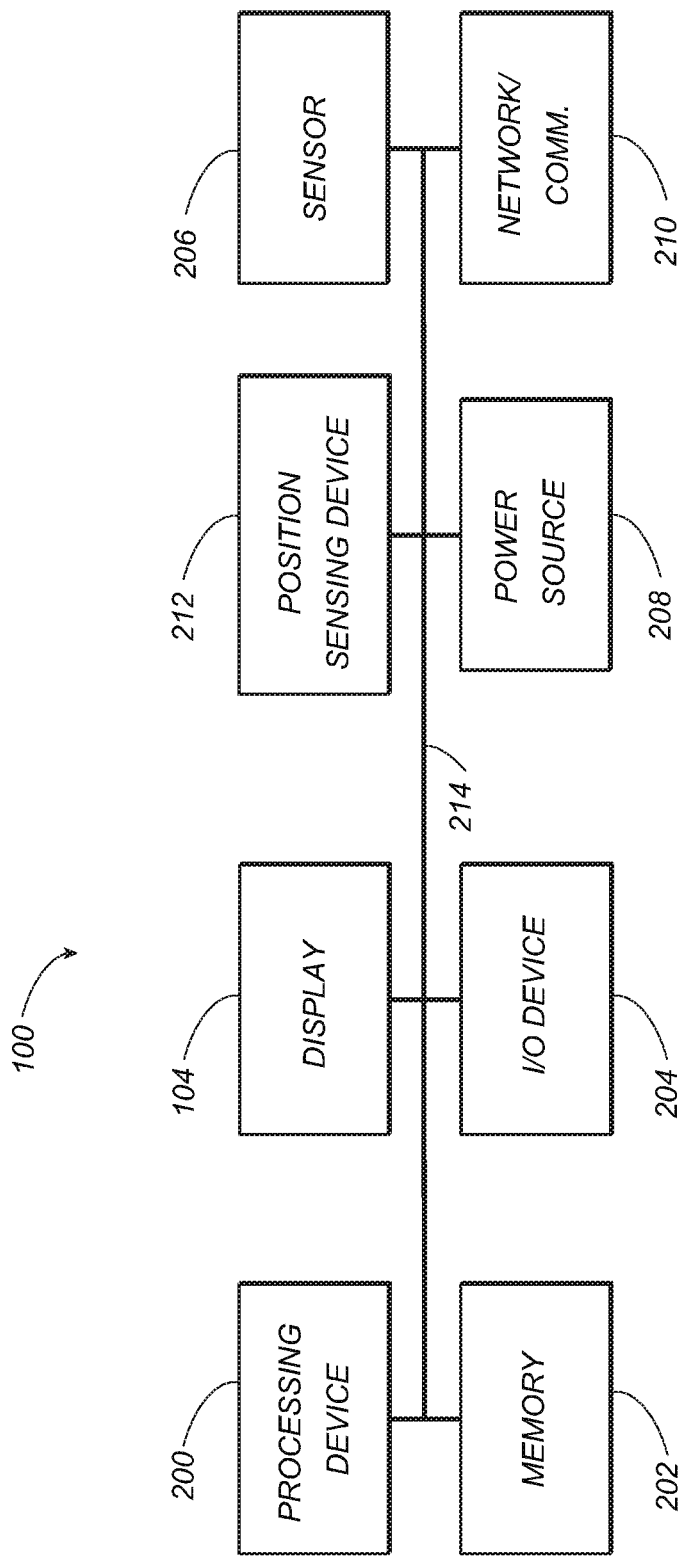
FIG. 2 is an illustrative block diagram of the wearable electronic device 100 shown in FIG. 1.

FIG. 2 is an illustrative block diagram of the wearable electronic device 100 shown in FIG. 1. The electronic device 100 can include the display 104, one or more processing devices 200, memory 202, one or more input/output (I/O) devices 204, one or more sensors 206, a power source 208, a network communications interface 210, and one or more position sensing devices 212. The display 104 may provide an image or video output for the electronic device 100. The display may also provide an input surface for one or more input devices, such as, for example, a touch sensing device and/or a fingerprint sensor. The display 104 may be substantially any size and may be positioned substantially anywhere on the electronic device 100.

The processing device 200 can control some or all of the operations of the electronic device 100. The processing device 200 can communicate, either directly or indirectly, with substantially all of the components of the electronic device 100. For example, a system bus or signal line 214 or other communication mechanisms can provide communication between the processing device(s) 200, the memory 202, the I/O device(s) 204, the sensor(s) 206, the power source 208, the network communications interface 210, and/or the position sensing device(s) 212. The one or more processing devices 200 can be implemented as any electronic device capable of processing, receiving, or transmitting data or instructions. For example, the processing device(s) 200 can each be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitably configured computing element or elements.

The memory 202 can store electronic data that can be used by the electronic device 100. For example, a memory can store electrical data or content such as, for example, audio and video files, documents and applications, device settings and user preferences, timing signals, signals received from the one or more position sensing devices, one or more pattern recognition algorithms, data structures or databases, and so on. The memory 202 can be configured as any type of memory. By way of example only, the memory can be implemented as random access memory, read-only memory, Flash memory, removable memory, or other types of storage elements, or combinations of such devices.

The one or more I/O devices 204 can transmit and/or receive data to and from a user or another electronic device. One example of an I/O device is button 106 in FIG. 1. The I/O device(s) 204 can include a display, a touch sensing input surface such as a trackpad, one or more buttons, one or more microphones or speakers, one or more ports such as a microphone port, and/or a keyboard.

The electronic device 100 may also include one or more sensors 206 positioned substantially anywhere on the electronic device 100. The sensor or sensors 206 may be configured to sense substantially any type of characteristic, such as but not limited to, images, pressure, light, touch, heat, biometric data, and so on. For example, the sensor(s) 206 may be an image sensor, a heat sensor, a light or optical sensor, a pressure transducer, a magnet, a health monitoring sensor, a biometric sensor, and so on.

The power source 208 can be implemented with any device capable of providing energy to the electronic device 100. For example, the power source 208 can be one or more batteries or rechargeable batteries, or a connection cable that connects the remote control device to another power source such as a wall outlet.

The network communication interface 210 can facilitate transmission of data to or from other electronic devices. For example, a network communication interface can transmit electronic signals via a wireless and/or wired network connection. Examples of wireless and wired network connections include, but are not limited to, cellular, Wi-Fi, Bluetooth, IR, and Ethernet.

The one or more position sensing devices 212 can each record the position, orientation, and/or movement of the electronic device. Each position sensing device can be an absolute or a relative position sensing device. The position sensing device or devices can be implemented as any suitable position sensor and/or system. Each position sensing device 212 can sense position, orientation, and/or movement along one or more axes. For example, a position sensing device 212 can be one or more accelerometers, gyroscopes, and/or magnetometers. As will be described in more detail later, a signal or signals received from at least one position sensing device are analyzed to determine which limb of a user is wearing the electronic device. The wearing limb can be determined by detecting and classifying the movement patterns while the user is wearing the electronic device. The movement patterns can be detected continuously, periodically, or at select times.

It should be noted that FIGS. 1 and 2 are illustrative only. In other examples, an electronic device may include fewer or more components than those shown in FIGS. 1 and 2. Additionally or alternatively, the electronic device can be included in a system and one or more components shown in FIGS. 1 and 2 are separate from the electronic device but included in the system. For example, a wearable electronic device may be operatively connected to, or in communication with a separate display. As another example, one or more applications can be stored in a memory separate from the wearable electronic device. The processing device in the electronic device can be operatively connected to and in communication with the separate display and/or memory. And in another example, at least one of the one or more position sensing devices 212 can be included in the band attached to the electronic device and operable connected to, or in communication with a processing device.

Figure 3B:
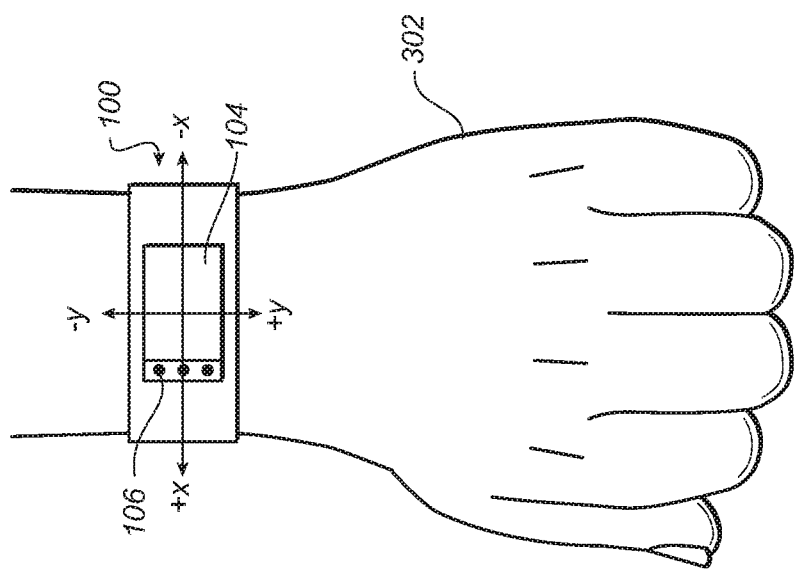
FIGS. 3A-3B illustrate a wearable electronic device on or near the right wrist and the left wrist of a user.
Figure 3A:
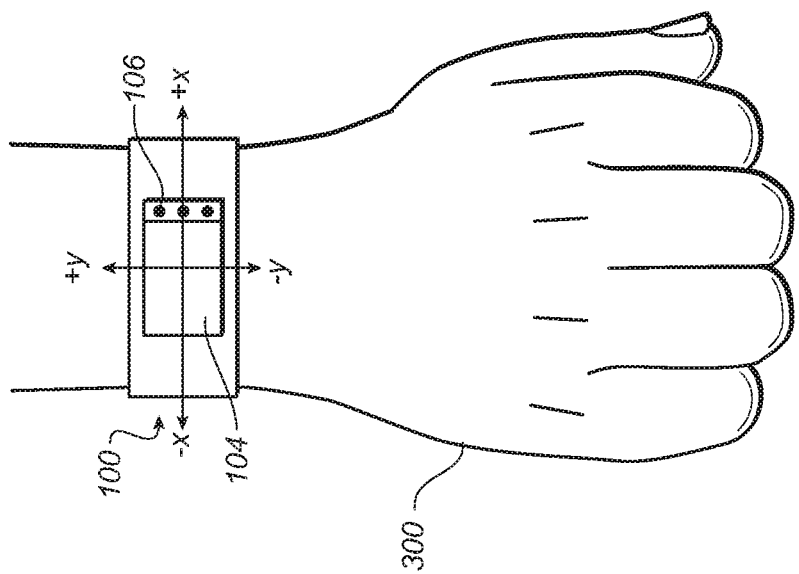

Embodiments described herein include an electronic device that is worn on a wrist of a user. However, as discussed earlier, a wearable electronic device can be worn on any limb, and on any part of a limb. FIGS. 3A-3B illustrate a wearable electronic device on or near the right wrist and the left wrist of a user. In some embodiments, a Cartesian coordinate system can be used to determine the positive and negative directions for the wearable electronic device 100. The determined positive and negative directions can be detected and used when classifying the movement patterns of the electronic device.

For example, the positive and negative x and y directions can be based on when the electronic device is worn on the right wrist of a user (see FIG. 3A). The positive and negative directions for each axis with respect to the electronic device is arbitrary but can be fixed once the position sensing device is mounted in the electronic device. In terms of the Cartesian coordinate system, the positive y-direction can be set to the position of the right arm being in a relaxed state and positioned down along the side of the body with the palm facing toward the body, while the zero position for the y-direction can be the position where the right arm is bent at substantially a ninety degree angle. The positive and negative directions can be set to different positions in other embodiments. A determination as to which limb is wearing the device can be based on the movement and/or positioning of the device based on the set positive and negative directions.

The buttons 106 shown in FIGS. 3A and 3B illustrate the change in the positive and negative directions of the x and y axes when the electronic device is moved from one wrist to the other. Once the x and y directions are fixed as if the electronic device is positioned on the right wrist 300 (FIG. 3A), the directions reverse when the electronic device is worn on the left wrist 302 (FIG. 3B). Other embodiments can set the positive and negative directions differently. For example, the positive and negative directions may depend on the type of electronic device, the use of the electronic device, and/or the positions, orientations, and movements that the electronic device may be subjected to or experience.

Figure 4:
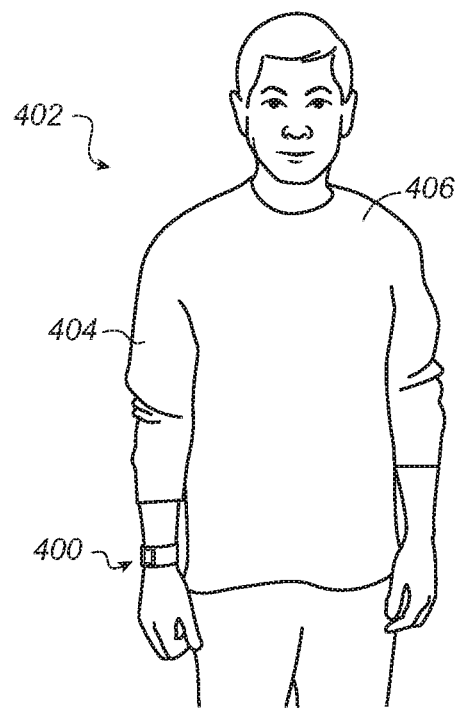
FIGS. 4-5 illustrate two positions of the wearable electronic device shown in FIG. 1 when worn on the right wrist of a user.
Figure 5:
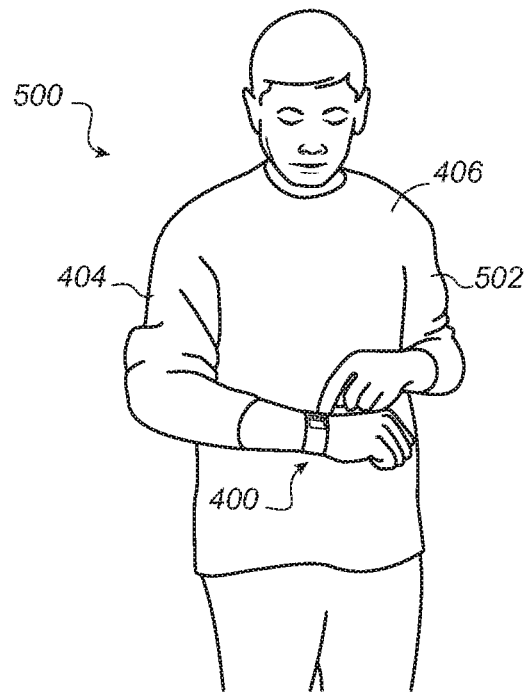

Referring now to FIGS. 4 and 5, there are shown two positions of the wearable electronic device shown in FIG. 1 when the electronic device is worn on the right wrist of a user. FIG. 4 illustrates a first position 402, where the right arm 404 of a user 406 is in a relaxed state with the arm down along the side of the body and the palm facing toward the body. FIG. 5 depicts a second position 500, where the right arm 404 is bent substantially at a ninety degree angle with the palm facing down toward the ground. The left arm 502 may also be bent to permit the left hand to interact with the electronic device.

Figure 6:
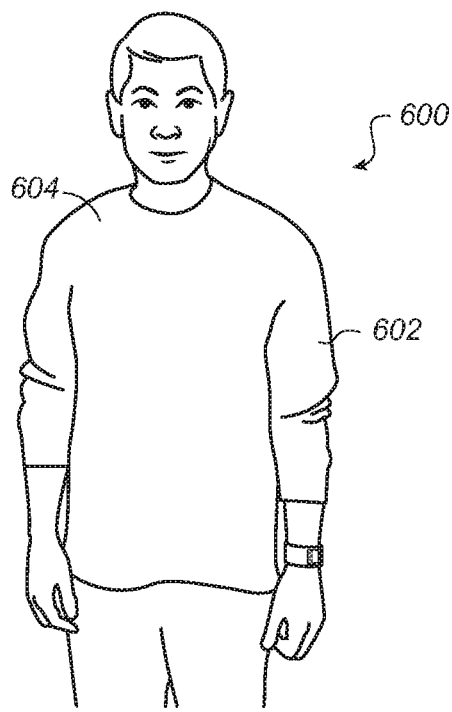
FIGS. 6-7 depict two positions of the wearable electronic device shown in FIG. 1 when worn on the left wrist of a user.
Figure 7:
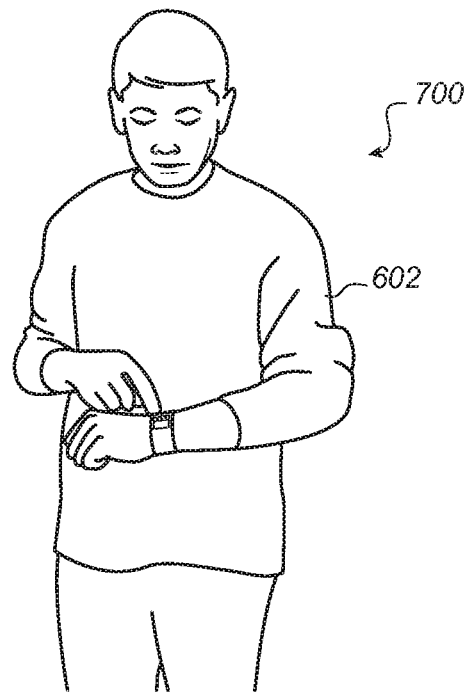

FIGS. 6 and 7 depict two positions of the wearable electronic device shown in FIG. 1 when the electronic device is worn on the left wrist of a user. FIG. 6 illustrates a third position 600, where the left arm 602 of the user 604 is in a relaxed state with the arm down along the side of the body and the palm facing toward the body. FIG. 7 shows a fourth position 700, where the left arm 602 is bent substantially at a ninety degree angle with the palm facing down toward the ground.

Figure 12:
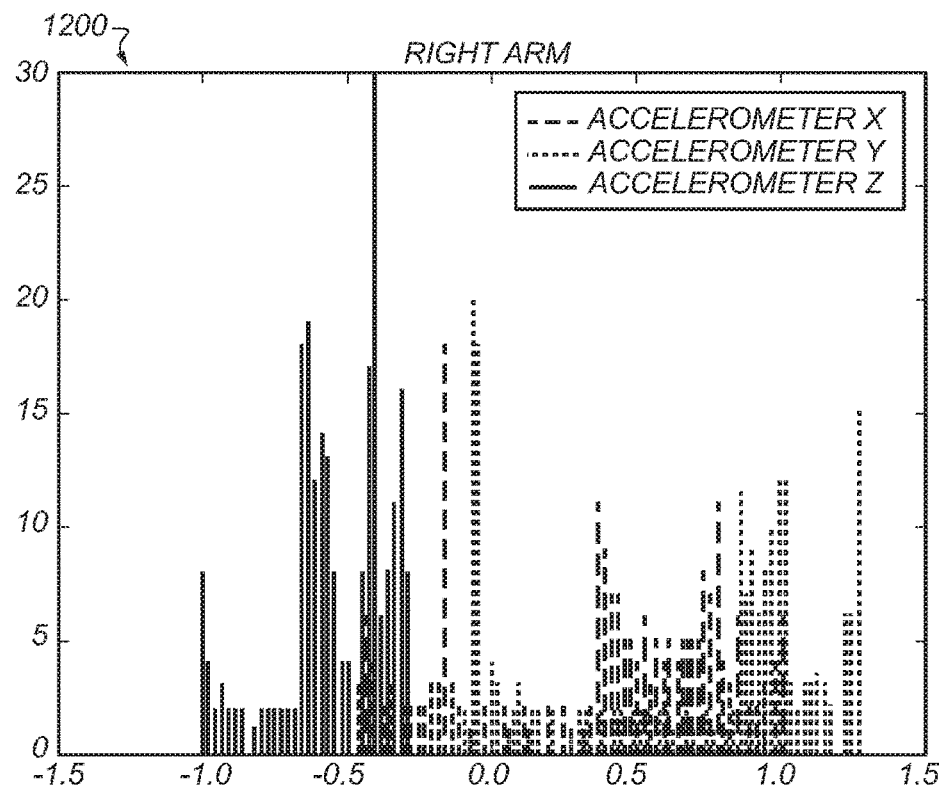
FIG. 12 illustrates example histograms of the x, y, and z axes data received from an accelerometer based on the two positions shown in FIGS. 4 and 5.
Figure 13:
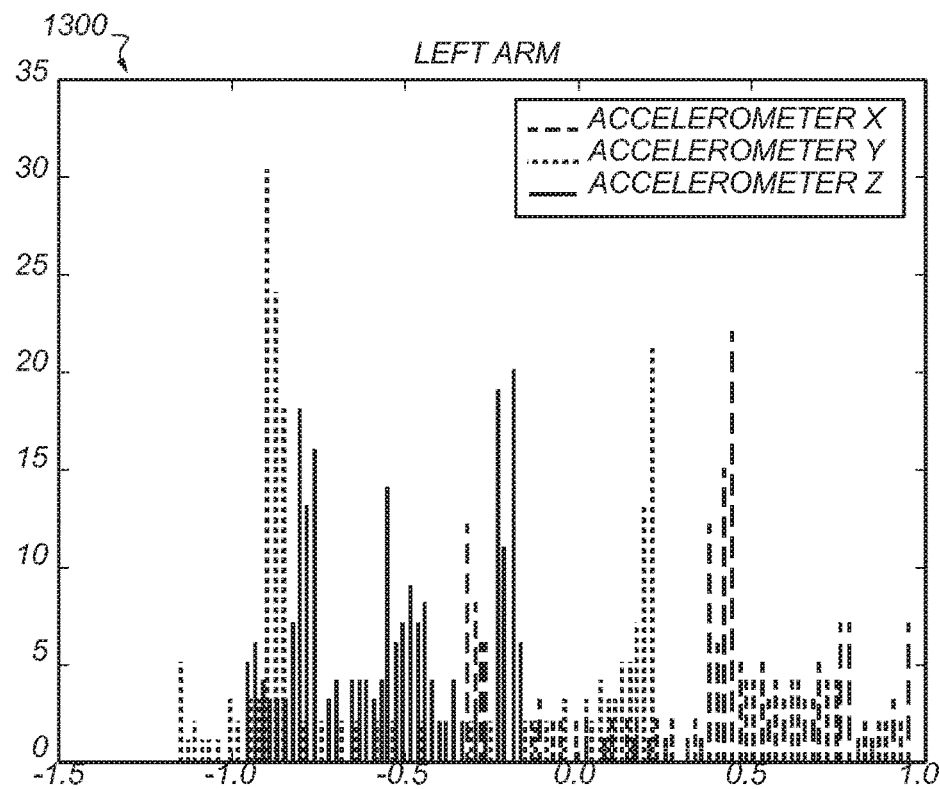
FIG. 13 depicts example histograms of the x, y, and z axes data obtained from an accelerometer based on the two positions shown in FIGS. 6 and 7.

In other embodiments, the limb the electronic device is affixed to may be positioned in any orientation or can move in other directions. For example, an arm of the user can be positioned at an angle greater to, or lesser than ninety degrees. Additionally or alternatively, a limb can be positioned or moved away from the body in any direction or directions. For example, a limb can be moved in front of and/or in back of the body, Embodiments described herein may process one or more signals received from at least one position sensing device and analyze the processed signals to determine which limb of the user is wearing the wearable electronic device. For example, a two-dimensional or three-dimensional plot of the signal or signals can be produced, as shown in FIGS. 8-11. Additionally or alternatively, a histogram based on the signal(s) can be generated, as shown in FIGS. 12 and 13. The plot(s) and/or histogram can be analyzed to determine the wearing limb of the electronic device. In one embodiment, a pattern recognition algorithm can be performed on the signal or signals or processed signal(s) to recognize a limb gesture and/or a limb position, and based on that determination, determine which limb or body part is wearing the electronic device.

Figure 8:
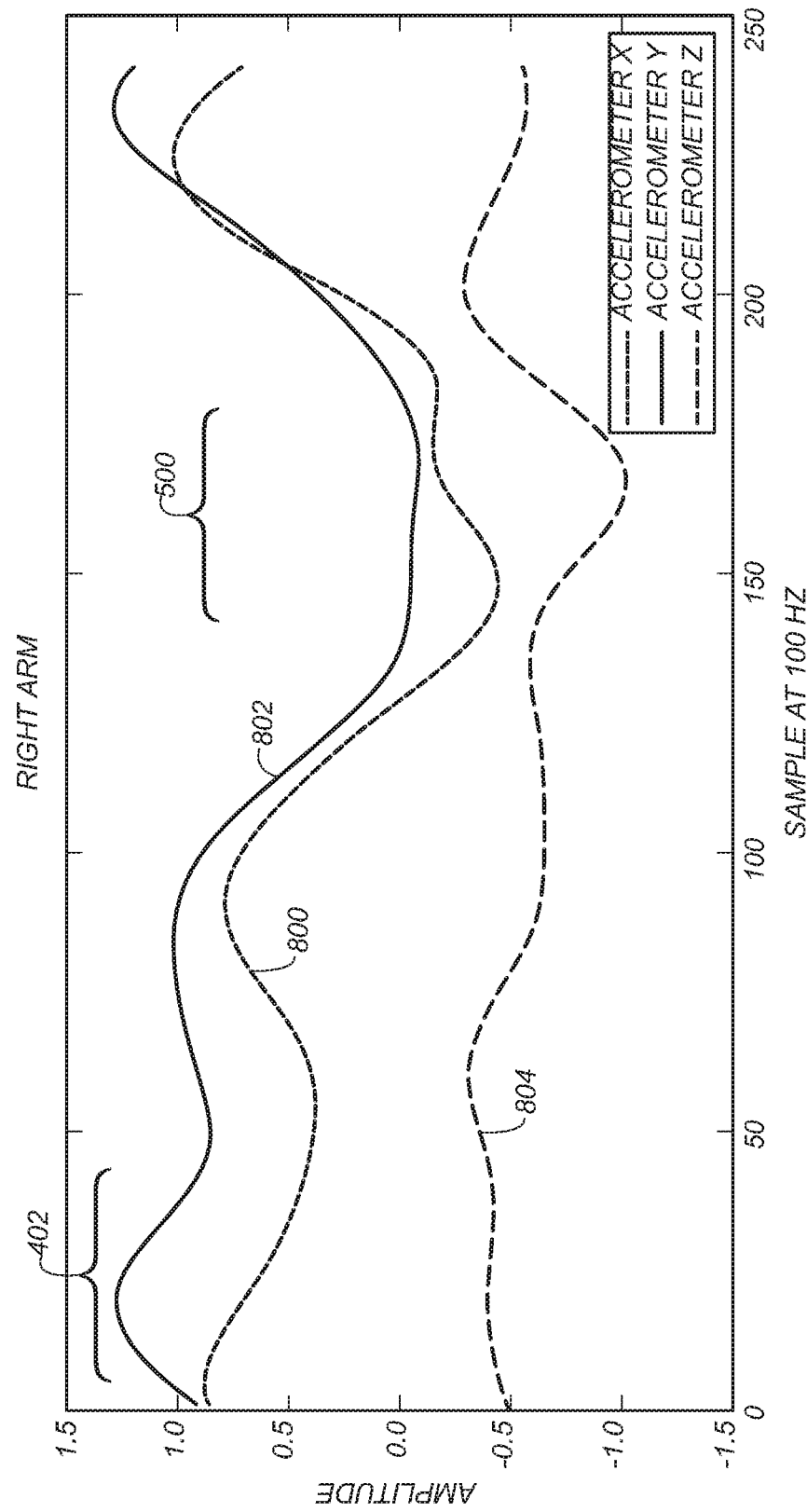
FIG. 8 illustrates example signals from an accelerometer based on the two positions shown in FIGS. 4 and 5.
Figure 9:
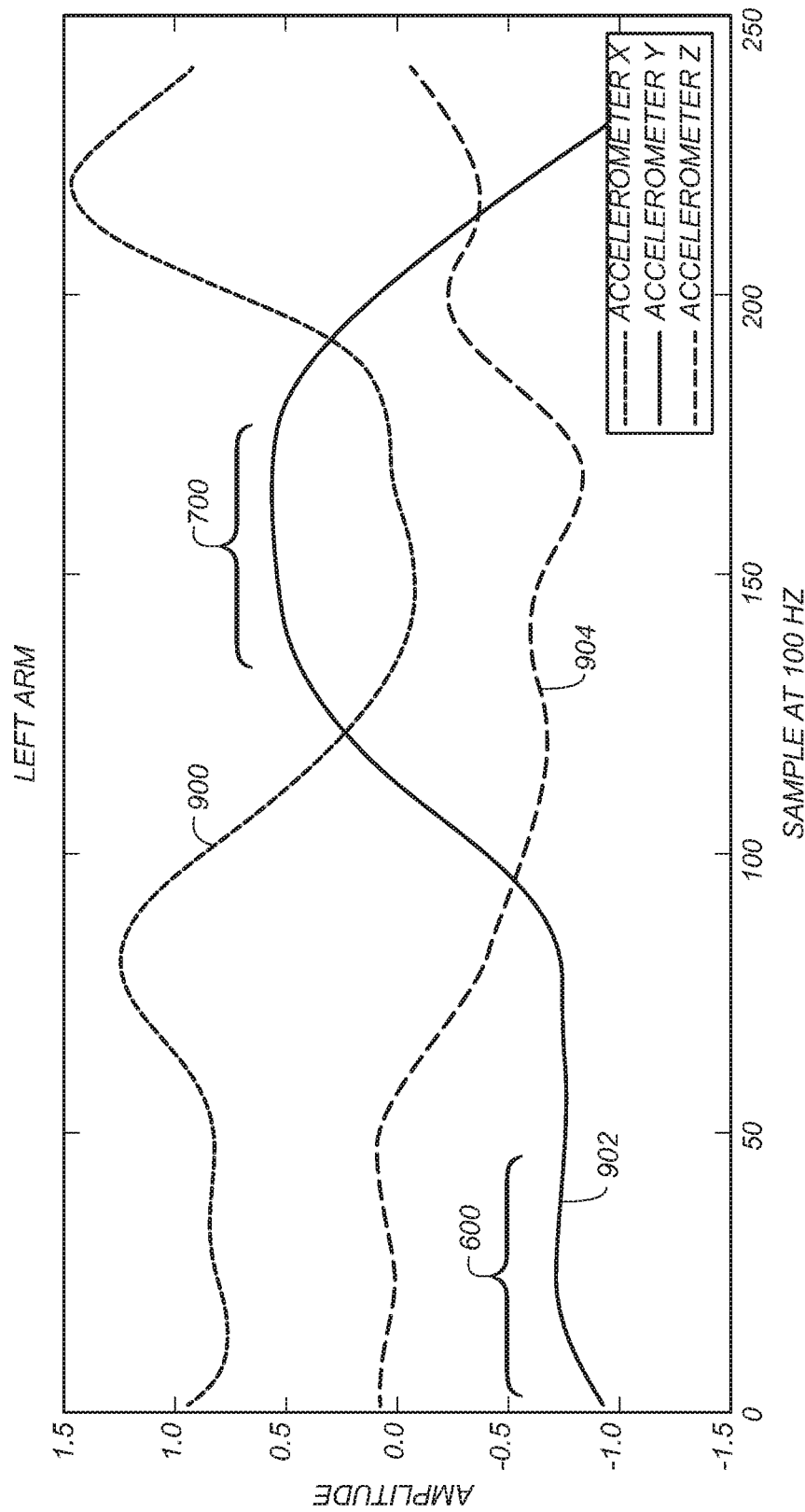
FIG. 9 depicts example signals from an accelerometer based on the two positions shown in FIGS. 6 and 7.

FIG. 8 depicts example signals from an accelerometer based on the two positions shown in FIGS. 4 and 5, while FIG. 9 illustrates example signals from the accelerometer based on the two positions shown in FIGS. 6 and 7. The accelerometer is configured as a three axis accelerometer and each plot is a signal measured along a respective axis as the arm is moved from one position to another position. For example, as shown in FIG. 3A, the electronic device can be moved from the first position 402 to the second position 500 and/or from the second position 500 to the first position 402 when the electronic device is worn on the right wrist. The plots in FIG. 8 depict the movement from the first position 402 to the second position 500. When on the left wrist as illustrated in FIG. 3B, the electronic device can be moved from the third position 600 to the fourth position 700 and/or from the fourth position 700 to the third position 600. FIG. 9 depicts the plots for the movement from the third position 600 to the fourth position 700.

In FIG. 8, plot 800 represents the signal measured along the x-axis, plot 802 the signal along the y-axis, and plot 804 the signal along the z-axis. In FIG. 9, plot 900 represents the signal produced along the x-axis, plot 902 the signal along the y-axis, and plot 904 the signal along the z-axis. The x and y axes correspond to the axes shown in FIGS. 3A and 3B. In reviewing the illustrative plot 802 when the electronic device 400 is worn on the right wrist, the value of y at the first position 402 is substantially plus one. At the second position 500, the value of y is substantially zero. Comparing plot 802 to plot 902 (device 400 is worn on the left wrist), the value of y at the third position 402 is substantially minus one, while the value of y at the fourth position is substantially zero. One or more of the plots shown in FIG. 8 or FIG. 9 can be analyzed to determine which limb of a user is wearing the electronic device.

It should be noted that since the electronic device can be positioned or moved in any direction, the values of the plots can be different in other embodiments.

Figure 10:
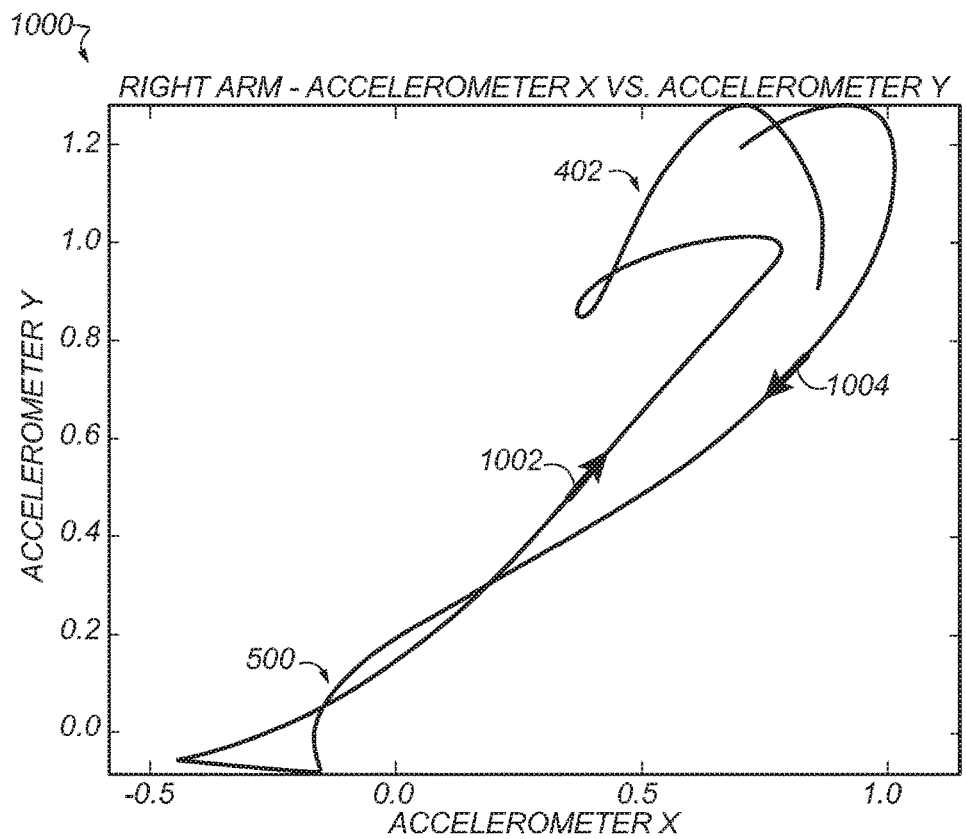
FIG. 10 illustrates an example plot of x and y axes data received from an accelerometer based on the two positions shown in FIGS. 4 and 5.

Referring now to FIG. 10, there is shown an example two-dimensional plot of samples obtained from an accelerometer based on the two positions shown in FIGS. 4 and 5, where the electronic device is worn on the right wrist. The signals received from the x-axis are plotted along the horizontal axis and the samples obtained from the y-axis are plotted along the vertical axis. Other embodiments can produce plots of the x and z axes, and/or the y and z axes. The plot 1000 represents a user moving the electronic device once from the first position 402 to the second position 500 and then back to the first position 402. Thus, the arrow 1004 represents the movement from the first position 402 to the second position 500, while the arrow 1002 represents the movement of the electronic device from the second position 500 to the first position 402.

Figure 11:
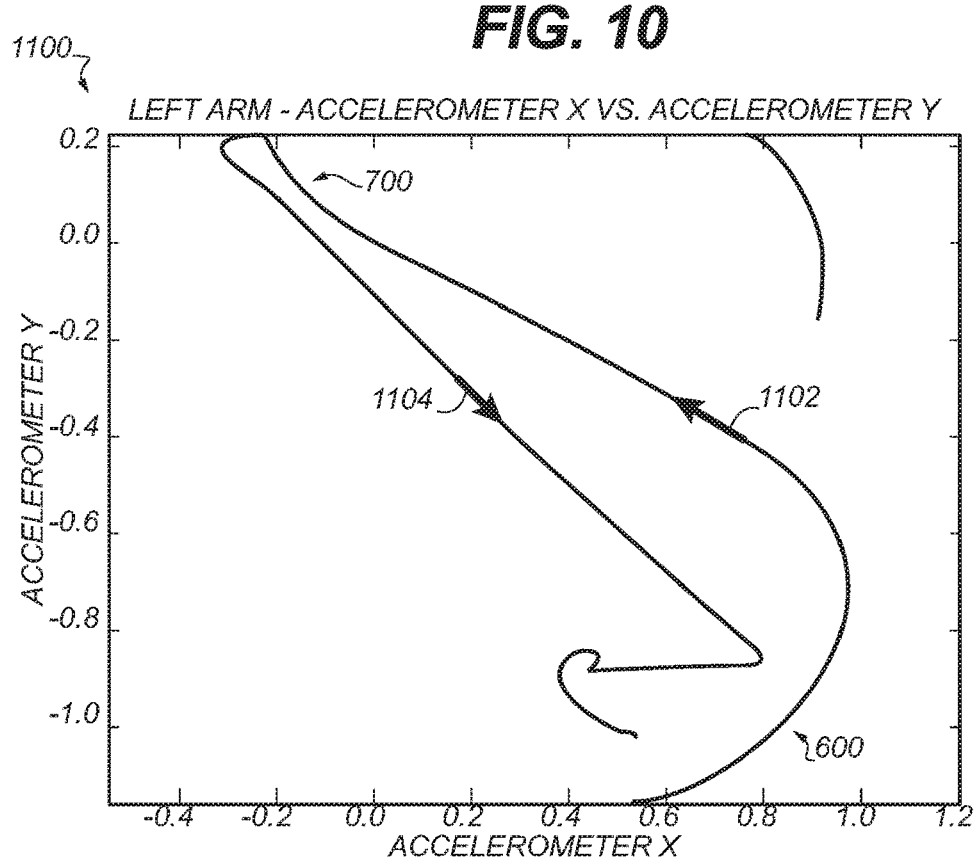
FIG. 11 depicts an example plot of x and y axes data obtained from an accelerometer based on the two positions shown in FIGS. 6 and 7.

In contrast, the plot in FIG. 11 represents a user moving the electronic device located on the left wrist once from the third position 600 to the fourth position 700 and then back to the third position 600. Like the plot 1000, the signals received from the x-axis are plotted along the horizontal axis and the samples obtained from the y-axis are plotted along the vertical axis. The arrow 1102 represents the movement from the third position 600 to the fourth position 700 and the arrow 1104 represents the movement of the electronic device from the fourth position 700 to the third position 600. The plot shown in FIG. 10 or FIG. 11 may be analyzed to determine which limb of a user is wearing the electronic device.

Referring now to FIG. 12, there is shown an example histogram of the samples obtained from an accelerometer based on the two positions shown in FIGS. 4 and 5. As described earlier, FIGS. 4 and 5 illustrate two positions of an electronic device that is worn on the right wrist. The histogram 1200 is a graphical representation of the distribution of the signals measured along the x-axis, the y-axis, and the z-axis. The histogram can be analyzed to determine which limb of a user is wearing the electronic device.

FIG. 13 illustrates an example histogram of the samples obtained from an accelerometer based on the two positions shown in FIGS. 6 and 7. As described earlier, FIGS. 6 and 7 depict two positions of an electronic device that is worn on the left wrist. Like the embodiment shown in FIG. 12, the histogram 1300 is a graphical representation of the distribution of the samples measured along the x-axis, the y-axis, and the z-axis, and the histogram can be analyzed to determine which limb of a user is wearing the electronic device.

Figure 14:
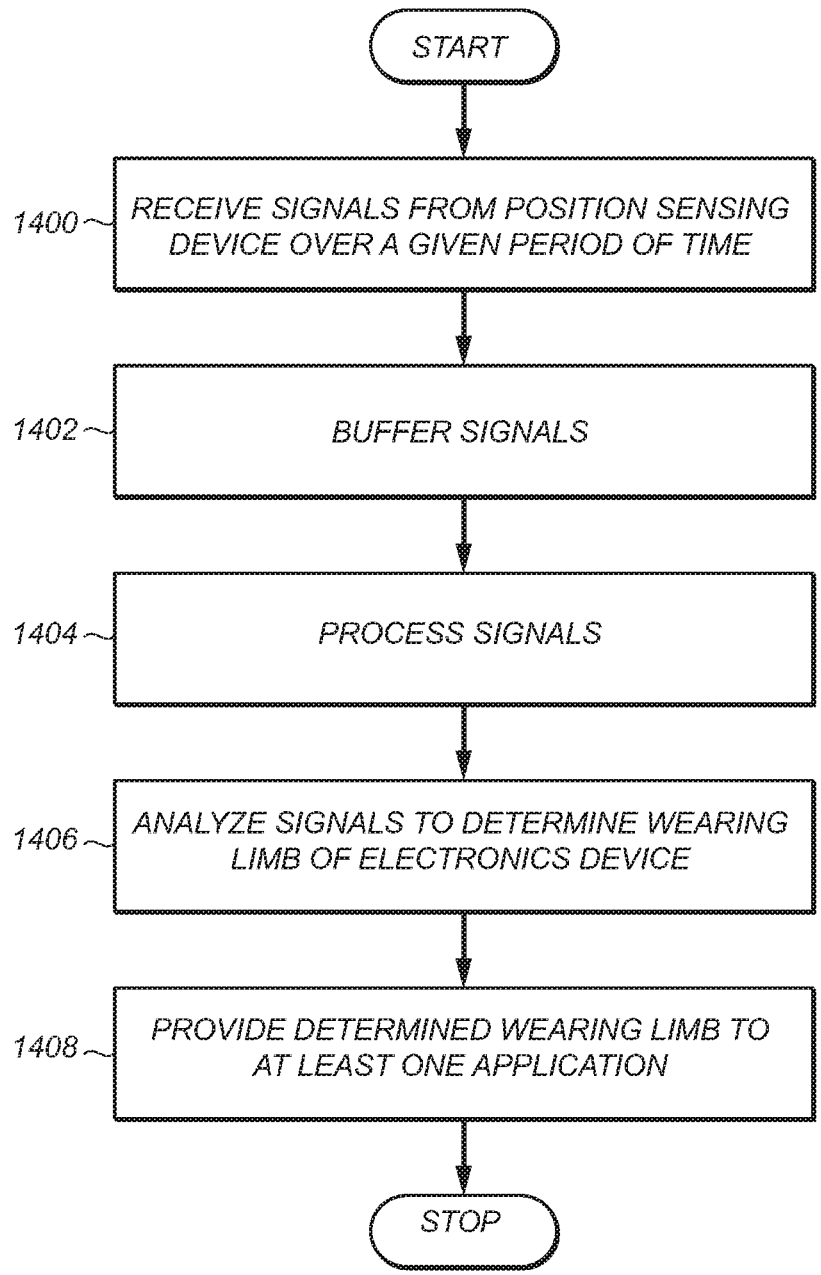
FIG. 14 is a flowchart of an example method for determining a limb wearing a wearable electronic device.

Referring now to FIG. 14, there is shown a flowchart of an example method for determining a limb wearing a wearable electronic device. Initially, at least one signal produced by a position sensing device is sampled over a given period of time (block 1400). For example, a signal produced by an accelerometer for the y-axis can be sampled for thirty or sixty seconds, or any other time period. As another example, multiple signals produced by a position sensing device can be sampled for a known period of time. The signal or signals can be sampled periodically or at select times. In some embodiments, the signal(s) can be sampled continuously.

The sampled signal or signals can optionally be buffered or stored in a storage device at block 1402. Next, as shown in block 1404, the signal(s) can be processed. As one example, the signal or signals can be plotted over the given period of time, an example of which is shown in FIGS. 8 and 9. As another example, the signal(s) can be represented graphically in a two-dimension or three-dimension plot. Examples of two-dimension plots are shown in FIGS. 10 and 11. Still other embodiments may process the samples to generate a histogram, examples of which are shown in FIGS. 12 and 13.

The signal or signals are then analyzed to determine which limb of a user is wearing the electronic device (block 1406). In one embodiment, a pattern recognition algorithm can be performed on the signals or processed signals to recognize one or more limb gestures and/or limb positions and classify them as from the right or left limb. Any suitable type of pattern recognition algorithm can be used to recognize the gestures and/or positions. For example, the signal or signals from at least one position sensing device can be classified using the Gaussian Mixture Models in two categories corresponding to the left and right limb (e.g., wrist) wearing the electronic device. The feature vector to be analyzed by the classifier may contain up to three dimensions if, for example, an accelerometer with three axes is used, or up to nine dimensions if an accelerometer, a gyroscope, and a magnetometer, each with 3 axes, are used.

The limb determined to be wearing the electronic device can then be provided to at least one application running on the electronic device, or running remotely and communicating with the electronic device (block 1408). The method can end after the information is provided to an application. For example, the determined limb information can be provided to an application that is performing biomedical or physiological data collection on the user. The data collection can relate to blood pressure, temperature, and/or pulse transit time. Additionally or alternatively, the application can be collecting data to assist in diagnosing peripheral vascular disease, such as peripheral artery disease or peripheral artery occlusion disease. Knowing which limb the data or measurements were collected from assists in diagnosing the disease.

Various embodiments have been described in detail with particular reference to certain features thereof, but it will be understood that variations and modifications can be effected within the spirit and scope of the disclosure. And even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

What is claimed is:

1. A method of detecting a gesture made by a user of a wearable electronic device, comprising:
    receiving at a processor of the wearable electronic device, over time, signals from at least one position sensing device included in the wearable electronic device;
    determining from the signals, at the processor, a movement pattern of the wearable electronic device, the movement pattern including movements in positive and negative directions with respect to a coordinate system; and
    identifying, at the processor, a gesture indicated by the movement pattern.

2. The method of claim 1, wherein identifying the gesture comprises performing a pattern recognition algorithm on the movement pattern.

3. The method of claim 1, wherein determining the movement pattern comprises producing a histogram based on the signals.

4. The method of claim 1, wherein determining the movement pattern comprises plotting the signals.

5. The method of claim 1, wherein one or more of the at least one position sensing device is included in a band of the wearable electronic device.

6. The method of claim 1, wherein the wearable electronic device comprises a device that provides time.

7. The method of claim 1, wherein the wearable electronic device comprises a health or fitness assistant.

8. The method of claim 1, wherein the wearable electronic device comprises a device that plays digital music.

9. The method of claim 1, wherein the determined movement pattern comprises movements of the wearable electronic device along two or more axes of the coordinate system.

10. The method of claim 9, wherein the two or more axes comprise three axes.

11. An electronic device wearable on a wrist of a user, comprising:
    a processor included within the electronic device; and
    one or more position sensing devices included within the electronic device and operatively connected to the processor; wherein,
    the processor is configured to:
        receive, over time, signals from the one or more position sensing devices;
        determine, from the signals, a movement pattern of the wearable electronic device, the movement pattern including movements in positive and negative directions with respect to a coordinate system; and
        identify a gesture indicated by the movement pattern.

12. The electronic device of claim 11, further comprising a memory adapted to store one or more pattern recognition algorithms, wherein the processor is configured to use the one or more pattern recognition algorithms to identify the gesture.

13. The electronic device of claim 12, wherein the processor is configured to identify the gesture by:
    reading a pattern recognition algorithm of the one or more pattern recognition algorithms from the memory; and
    applying the pattern recognition algorithm to the movement pattern.

14. The electronic device of claim 11, wherein the electronic device comprises a health or fitness assistant.

15. The electronic device of claim 11, wherein the electronic device comprises a device that provides time.

16. The electronic device of claim 11, wherein at least one of the one or more position sensing devices comprises at least one: of an accelerometer, a magnetometer, or a gyroscope.

17. The electronic device of claim 11, wherein an axis of the coordinate system is substantially aligned with a relaxed state of an arm of the user, which arm includes the wrist on which the electronic device is worn.

18. The electronic device of claim 11, wherein the processor is configured to determine, using the identified gesture, whether the electronic device is worn on a left wrist or a right wrist.

19. An electronic device wearable on a wrist of a user, comprising:
    an enclosure;
    a processor mounted within the enclosure;
    a display mounted to the enclosure and operatively connected to the processor; and a set of position sensing devices mounted within the enclosure and operatively connected to the processor; wherein, the processor is configured to:

determine, from a set of outputs of the set of position sensing devices, movements of the electronic device in positive and negative directions along two or more axes; and identify a gesture of the user using the determined movements.

20. The electronic device of claim 19, wherein the two or more axes comprise three axes.

\* \* \* \* \*